United States Patent
El-Andaloussi et al.

(10) Patent No.: US 9,803,219 B2
(45) Date of Patent: Oct. 31, 2017

(54) ADENOVIRUS DERIVED HELPER VIRUS FOR ENHANCING RECOMBINANT PARVOVIRUS PRODUCTION

(71) Applicant: DEUTSCHES KREBSFORSCHUNGSZENTRUM, Heidelberg (DE)

(72) Inventors: Nazim El-Andaloussi, Heidelberg (DE); Antonio Marchini, Heidelberg (DE); Jean Rommelaere, Heidelberg (DE); Barbara Leuchs, Heidelberg (DE); Max Endele, Wilhelmsfeld (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days.

(21) Appl. No.: 13/627,554

(22) Filed: Sep. 26, 2012

(65) Prior Publication Data
US 2013/0089523 A1 Apr. 11, 2013
US 2017/0073704 A9 Mar. 16, 2017

Related U.S. Application Data

(63) Continuation-in-part of application No. PCT/EP2011/001493, filed on Mar. 24, 2011.

(30) Foreign Application Priority Data

Mar. 26, 2010 (EP) .................................. 10003296

(51) Int. Cl.
| | | |
|---|---|---|
| *A01N 63/00* | (2006.01) | |
| *C12N 15/864* | (2006.01) | |
| *C07K 14/005* | (2006.01) | |
| *C12N 15/86* | (2006.01) | |
| *A61K 35/13* | (2015.01) | |
| *A61K 48/00* | (2006.01) | |

(52) U.S. Cl.
CPC ........ *C12N 15/8645* (2013.01); *C07K 14/005* (2013.01); *C12N 15/86* (2013.01); *A61K 35/13* (2013.01); *A61K 48/00* (2013.01); *C12N 2710/10344* (2013.01); *C12N 2750/14143* (2013.01); *C12N 2750/14343* (2013.01); *C12N 2750/14344* (2013.01); *C12N 2750/14351* (2013.01); *C12N 2750/14352* (2013.01)

(58) Field of Classification Search
CPC ............ C12N 2750/14011; C12N 2750/14311
See application file for complete search history.

(56) References Cited

U.S. PATENT DOCUMENTS

| | | | |
|---|---|---|---|
| 7,115,391 B1 | 10/2006 | Chen | |
| 7,267,825 B1 * | 9/2007 | Rommelaere | C07K 14/523 424/233.1 |
| 7,485,458 B2 | 2/2009 | Colosi | |

FOREIGN PATENT DOCUMENTS

| | | | | |
|---|---|---|---|---|
| DE | WO 00/22151 | * | 4/2000 | .......... C12N 15/864 |
| JP | A-2001-517071 | | 10/2001 | |
| JP | A-2003-511037 | | 3/2003 | |
| WO | WO 01/25462 | * | 4/2001 | ............ C12N 15/86 |
| WO | WO 01/25462 A1 | | 4/2001 | |
| WO | WO 03/061582 | | 7/2003 | |

OTHER PUBLICATIONS

Bowles et al. (2003, J. Virology, vol. 77(1), pp. 423-432).*
Ponnazhagan et al. (1998, J. Virology, vol. 72(6), pp. 5224-5230).*
Guan et al. (2009, J. Virology, vol. 83(18), pp. 9541-9553).*
Ledinko et al. (1968, J. Virology, vol. 2(2), pp. 155-156).*
A. Brandenburger, et al., A Novel Packaging System for the Generation of Helper-Free Oncolytic MVM Vector Stocks, Gene Therapy (1996) vol. 3, p. 927-931.
Siew Chiat Cheong, et al., A Novel Method for the Titration of Recombinant Virus Stocks by ELISPOT Assay, Journal of Virological Methods (2003) vol. 109, p. 119-124.
Roy F. Collaco, et al., A Helper Virus-Free Packaging System for Recombinant Adeno-Associated Virus Vectors, Gene (1999) vol. 238, p. 397-405.
N. El-Andaloussi, et al., Novel Adenovirus-Based Helper System to Support Production of Recombinant Parvovirus, Cancer Gene Therapy (2011) vol. 18, p. 240-249.
M. Enderlin, et al., TNF-α and the IFN-β-Inducible Protein 10 (IP-10/CXCL-10) Delivered by Parvoviral Vectors Act in Synergy to Induce Antitumor Effects in Mouse Glioblastoma, Cancer Gene Therapy (2009) vol. 16, p. 149-160.
D. Grimm, et al., Novel Tools for Production and Purification of Recombinant Adenoassociated Virus Vectors, Human Gene Therapy (1998) vol. 9, p. 2745-2760.
J. Kestler, et al., cis Requirements for the Efficient Production of Recombinant DNA Vectors Based on Autonomous Parvoviruses, Human Gene Therapy (1999) vol. 10, p. 1619-1632.
L. Kruger, et al., Augmented Transgene Expression in Transformed Cells Using a Parvoviral Hybrid Vector, Cancer Gene Therapy (2008) vol. 15, p. 252-267.
X. Xiao, et al., Production of High-Titer Recombinant Adeno-Associated Virus Vectors in the Absence of Helper Adenovirus, Journal of Virology (1998) vol. 72, No. 3, p. 2224-2232.
H. Zhang, et al., Recombinant Adenovirus Expressing Adeno-Associated Virus Cap and Rep Proteins Supports Production of High-Titer Recombinant Adeno-Associated Virus, Gene Therapy (2001) vol. 8, p. 704-712.
Australian Examination Report for AU Patent Application. No. 2011231998 dated Jun. 11, 2014.
Office Action issued for Japanese patent application 2013-501673 dated Jan. 20, 2015 and English translation thereof.

(Continued)

*Primary Examiner* — Peter Paras, Jr.
*Assistant Examiner* — David A Montanari
(74) *Attorney, Agent, or Firm* — Vedder Price P.C.; Thomas J. Kowalski; Deborah L. Lu (57) ABSTRACT

Described is an adenovirus derived helper virus which may comprise the adenoviral DNA sequences for E2a, S4 (orf6), the VA1 RNA gene, and the parvovirus VP capsid gene unit. Also described is a method of efficiently preparing a recombinant parvovirus (particle) which is based on the use of various adenoviral derived helper viruses/vectors.

9 Claims, 7 Drawing Sheets

(56) References Cited

OTHER PUBLICATIONS

Collaco RF, Cao X, Trempe JP. A helper virus-free packaging system for recombinant adeno-associated virus vectors. Gene. Oct. 1, 1999;238(2):397-405.

Xiao X, Li J, Samulski RJ. Production of high-titer recombinant adeno-associated virus vectors in the absence of helper adenovirus. J Virol. Mar. 1998;72(3):2224-32.

Zhang HG, Wang YM, Xie JF, Liang X, Hsu HC, Zhang X, Douglas J, Curiel DT, Mountz JD. Recombinant adenovirus expressing adeno-associated virus cap and rep proteins supports production of high-titer recombinant adeno-associated virus. Gene Ther. May 2001;8(9):704-12.

\* cited by examiner

Schematic map of the Ad-VP helper plasmid

ADENOVIRUS DERIVED HELPER VIRUS FOR ENHANCING RECOMBINANT PARVOVIRUS PRODUCTION

RELATED APPLICATIONS AND INCORPORATION BY REFERENCE

This application is a continuation-in-part application of international patent application Serial No. PCT/EP2011/001493 filed 24 Mar. 2011, which published as PCT Publication No. WO 2011/116974 on 29 Sep. 2011, which claims benefit of European patent application Serial No. EP10003296 filed 26 Mar. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to an adenovirus derived helper virus which may comprise the adenoviral DNA sequences for E2a, E4 (orf6), the VAI RNA gene, and the parvovirus VP capsid gene unit. The present invention also relates to a method of efficiently preparing a recombinant parvovirus (particle) which is based on the use of various adenoviral derived helper viruses/vectors.

BACKGROUND OF THE INVENTION

Parvoviruses are icosahedral, single stranded, DNA viruses. Their genome is about 5.1 kilobases and includes the P4 and P38 promoters, which drive the expression of non structural (NS1 and NS2) and structural (VP1 and VP2)) proteins, respectively. Parvoviruses belong to the Parvovirinae family, together with Dependo- and Erythroviruses. The Dependoviruses include the adeno-associated viruses (AAV). These viruses, as the name suggests, are dependant on a helper virus, like adenovirus, for a productive infection cycle [1]. On the other hand, Erythroviruses and Parvoviruses are autonomous; they are able to complete their productive cycle without a helper virus. Erythroviruses include B19, known to be pathogenic to humans.

Rodent parvoviruses are non-pathogenic for humans and show oncotropic and oncolytic properties that make them very attractive agents for cancer therapy. To further enhance their intrinsic anti-neoplastic ability, recombinant viruses have been generated to deliver anti-tumour transgenes to cancer cells. The strategy consists of replacing the VP capsid genes with a particular transgene [2]. The vectors retain the NS1/2 coding sequence (under the control of the parvoviral P4 promoter) and the parvoviral genome telomeres which are necessary for viral DNA amplification and packaging. The transgene of interest is generally expressed under the control of the P38 promoter, which is strongly trans-activated by the NS1 protein. Production of the recombinant viruses can only occur in producer cells, providing the VP proteins in trans. The deletion of the capsid coding region in the viral genome gives the opportunity to insert transgenes up to approximately 2500 nt, although large VP deletions reduce production titers significantly, probably due to the suppression of important virus packaging cis-acting elements [2]. The recombinant parvoviral vectors generated in this way are replication-defective, providing an additional therapeutic safety advantage in comparison to their replicative counterparts. Examples of transgenes successfully transduced by recombinant parvoviruses include toxic genes, such as herpes simplex virus thymidine kinase (e.g. used in combination with the prodrug ganciclovir) [3] or Apoptin [4]. Virions expressing these transgenes have improved anti-neoplastic activities in comparison to wild type viruses. Recombinant parvoviruses encoding immunomodulatory genes such as cytokines or chemokines, like Interleukin-2 (IL-2) or Monocyte Chemotactic Protein 1 or 3 (MCP-1) [5-8], Interferon-γ-inducible protein (IP-10) [9] have been also generated. These virions induce potent antitumoral bystander effects in various in vitro and in vivo tumor models. Recently, antitumoral synergistic effects were observed using a combination of recombinant viruses transducing Tumor Necrosis Factor-α (TNF-α) and IP-10 [10].

The helper activities of adenovirus towards AAV replication have been studied extensively. The adenoviral E1A protein is essential for the activation of AAV gene expression by binding and activating the AAV-2 P5 rep promoter [12]. Similarly, E2A, another adenoviral protein, activates the AAV-2 PS promoter transcription [13]. E2A also appears to cooperate with virus associated RNA I (VAI RNA) to enhance the translation of AAV-2 RNAs [14]. The adenoviral E4 (orf6) enhances the conversion of single-stranded recombinant AAV-2 genomes into double-stranded genomes, a rate-limiting step of viral DNA-replication both in vitro and in vivo [15]. VAI RNA can also support AAV-5 replication. It has been described that VAI RNA physically interacts with the double-stranded RNA-activated protein kinase (PKR), which would otherwise elicit an antiviral immune response blocking viral protein production [16].

Studies with recombinant AAV-2 have confirmed that a small subset of adenoviral genes is sufficient for the helper effect. In HEK 293 cells, which provide the E1 gene in trans, the minimal set of genes for efficient recombinant AAV-2 production is E2a, E4 (orf6) and the VAI RNA gene [17, 18]. A helper plasmid named pXX6, containing this set of genes, is currently used for the production of adenovirus-free recombinant AAV-2 [18]. This plasmid sustains AAV-2 production in a similar way as infectious adenovirus [18, 19]. Adenovirus genes (E2a, E4orf6, and VAI RNA genes) also allow human erythrovirus B19 DNA replication and viral production in HEK 293 cells, that would otherwise be non-permissive for B19 [20].

The interaction between adenovirus and autonomous parvoviruses has however remained less explored. H-1 parvovirus replication in secondary cultures of normal human embryonic lung cells is not initiated, unless they are co-infected with adenovirus serotype 12 as a helper virus [21]. In addition, adenovirus serotype 2 induces an increase of MVMp parvovirus DNA replication and relocalizes MVMp DNA from host nucleoli to adenovirus replication factories in HeLa cells (22).

One major challenge in the development and optimization of recombinant parvoviruses (rec.PVs) for clinical applications is to increase the amount of viruses being produced. Due to their non-proliferative nature, their production depends solely on the transfection efficiency of the parvoviral genomic components into the packaging cell lines (normally human embryonic kidney cells, HEK 293 or 293T). Also the use of packaging cell lines constitutively expressing the VP proteins did not significantly improve the production of recombinant parvoviruses [11]. It remains of high importance to develop means to increase recombinant parvovirus production.

Thus, the problem on which the present invention is based was to provide a means for increasing the efficiency of recombinant parvovirus production.

Citation or identification of any document in this application is not an admission that such document is available as prior art to the present invention.

SUMMARY OF THE INVENTION

This technical problem is solved by providing the embodiments characterized in the claims. It has been surprisingly found that also the production of recombinant parvoviruses may benefit from the help of adenovirus genes. Production of recombinant parvoviruses is classically made in HEK 293T producer cells by transfecting them with the recombinant parvoviral genome and a plasmid carrying the capsid VP genes. The protocol in use yields very low titers of recombinant parvoviruses, ranging from 0.1 to 0.5 transduction unit (TU) per production cell, under the best conditions. Furthermore, due to differences in plasmid transfection efficiency there is also a high variability of the obtained titers. The viruses generated in this manner are replication defective, but contain a small fraction of replication competent viruses (RCVs) reconstituted through homologous recombinations between viral genomes and capsid genes [11]. These RCVs are unwanted contaminants of the final viral stocks and it is therefore important to limit their occurrence during recombinant parvovirus production.

In the experiments resulting in the present invention, the efficiency of recombinant parvovirus production using adenovirus genes that were introduced into the cells, either by transfecting the production cells with an adenovirus-derived plasmid pXX6 or infecting them with recombinant Adenovirus-5 (Ad-5) could be significantly increased. Using the new protocol, more than 10 fold higher titers in a shorter time frame (2 rather than 3 days) were reached. The percentage of RCV generated is comparable to the adenovirus-free protocol. In light of these results, a novel replication-defective recombinant Ad-5 vector harboring the parvovirus capsid gene unit (Ad-VP helper) was generated. With this helper virus, recombinant parvoviruses could be generated in other producer cells such as NB324K (NBK) and higher viral titers were produced without affecting the quality of the recombinant virus. Importantly, the use of Ad-VP helper allows one to bypass the transfection step. The process may be standardized, is reproducible and both production times and costs are reduced.

In summary:

The use of adenovirus 5 derived vectors, e.g., pXX6 (supplied by transfection) and the Ad5ΔE1ΔE3, (supplied by transfection and through infection in the form of Ad5ΔE1ΔE3-CMV/GFP recombinant virus), enhance by more than 10 fold the production of recombinant parvoviruses in HEK 293T cells.

The increase in production provided by adenovirus vectors, is independent from the mode of delivery of the recombinant parvoviruses, (plasmid transfection or viral infection), as well as size and nature of the parvoviral transgene in HEK 293T cells.

pXX6 accelerates the production of recombinant parvovirus and shortens the production time from 3 to 2 days.

pXX6 significantly increases and accelerates parvovirus DNA replication in HEK 293T cells.

pXX6 does not promote the generation of unwanted Replication Competent Virus (RCV); the levels of RCV obtained using the pXX6-based protocol are as low as those obtained using conventional approaches.

The Ad-VP helper virus containing the Ad helper genes as well as the parvovirus capsid gene unit allows amplification of recombinant parvoviruses, without the need of a transfection step, via infection of Ad-VP helper virus in combination with the recombinant parvovirus of choice. This reduces significantly the production time and costs (regarding, for example transfection reagents and personnel).

Moreover, it overcomes previous limitations in the choice of the packaging cell line used, as it renders possible the use of cell lines that are difficult to transfect but are good producers of PVs, e.g. NBK cells. This allows large-scale production of recombinant parvovirus e.g. in bioreactors.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

HEK 293T cells, seeded in 6 cm dishes, were transfected with prec. PV-GFP and pCMV/VP to produce recombinant parvoviruses. Simultaneously, they were either co-transfected or not with the adenovirus derived plasmid pXX6. Three days post transfection, cells were harvested together with their medium and lysed via three freeze and thaw cycles. Equal volumes of crude virus extracts were applied to fresh NBK cells in a transduction assay, as described in Materials and Methods section.

A: Representative example of micrographs from the transduction assay, showing GFP positive cells from confluent cellular layers. Micrographs were taken with the same camera settings suggesting that different scored numbers of green cells corresponds to a different virus inoculum.

B: Western Blot analysis. Triplicate samples from the transduction assay were pooled and proteins were extracted. 5 μg of proteins were separated by SDS-PAGE. Immunoblots were performed using anti-NS1, -GFP and -Actin antibodies (used as a loading control). neg., negative control (non-transfected cells).

C: Quantification of the transduction assays. Cells were transfected with prec.PV-GFP, pCMV/VP in combination with the indicated plasmids, or without any additional DNA (−). pXX6 or pAd5ΔE1ΔE3 were used as helper plasmids and pFRT/lacZeo was used as a control filler DNA with the same quantities, as indicated on the figure. Bars represent the mean of three replicates with relative standard deviations. Values above data bars indicate fold changes in virus titer production, obtained in presence of adenoviral helper plasmids in comparison to negative control. TU, transduction unit.

FIG. 2: Recombinant parvovirus production is enhanced by pXX6 adenovirus-derived plasmid HEK 293T cells, seeded in 175 cm$^2$ flasks, were transfected with prec.PV-GFP, pCMV/VP with or without pXX6. Three days post-infection, cells were collected and resuspended in 0.5 ml vTE buffer (50 mM Tris-HCl [pH 8.3], 0.5 mM EDTA) and lysed via three freeze and thaw cycles. Crude virus extracts were used in different assays to determine virus titers. Bars represent the means of different replicates with relative standard deviations. Values above data bars show fold changes in virus production in presence versus absence of pXX6. Virus titers are given in Vg/ml, as measured through parvovirus specific quantitative PCR (Q-PCR), TU/ml as a result of a transduction assay or RU/ml through a parvovirus specific hybridization assay. Produced replicative competent parvoviruses were measured by plaque assay and the results were expressed as a ratio of produced PFU versus produced TU. Vg, viral genome; TU, transduction unit; RU, replication unit; PFU, plaque forming unit.

FIG. 3: Adenoviral helper plasmids or recombinant Ad-GFP virus enhance the production of recombinant parvoviruses harboring long transgene HEK 293T cells, seeded in 6 cm dishes, were transfected with a mixture of prec.PV-luciferase and pCMVNP, with the addition of either pXX6 or pVAE2AE4-5 as helper plasmids, or without any additional DNA (−). In parallel, 1 h post transfection of parvovirus plasmids, a set of dishes was infected with purified recombinant Ad5ΔE1ΔE3-CMV/GFP (Ad-GFP) at the indicated MOI (GFU/cell). Three days later, cells were treated as indicated in FIG. 1 legend. Crude virus extracts were used to infect NBK cells, and 48 h later, total NBK extracts were used for luciferase assays, as indicated in Material and Methods section. Bars represent the mean of three with their relative standard deviations. Values replicates above data bars show fold changes in luciferase production compared to the negative control. GFU: green fluorescent unit. RLU, relative luciferase unit.

HEK 293T cells, seeded in 10 cm dishes, were transfected with prec.PV-GFP, pCMV/VP with or without the pXX6 plasmid. After transfection, cells were collected in their medium at the indicated time. Half of the harvest was lysed as previously described and used for transduction assays, while the other half was used for Southern Blot analysis.

A: Result of the transduction assay. Bars represent the mean values of three replicates with their relative standard deviations. Values above data bars show fold changes in virus titers production in presence of pXX6 compared to its absence.

B: Southern Blot analysis. Viral DNA was extracted from crude DNA cell lysates separated through a 1% agarose gel electrophoresis and transferred onto a nylon membrane. The membrane was incubated with a parvovirus specific [$^{32}$P] labeled DNA probe and subjected to autoradiography. Neg., negative control (non-transfected cells).

FIG. 5: pXX6 increases recombinant parvovirus production in a transfection/infection-based protocol HEK 293T cells, seeded in 6 cm dishes, were transfected with pCMV/VP, +/−pXX6 and then infected with rec.PV-GFP. Three days later, cells were collected in their medium and lysed via three freeze and thaw cycles. Crude virus extracts were used to determine virus titers by transduction assay as previously described. Shown are total input and output virus amounts. Values above data bars show amplification rates of the input virus during the production. TU, transduction unit.

FIG. 6: Production of different recombinant parvoviruses using recombinant Ad-VP helper virus A: NBK cells, seeded in 6 well plates, were infected with purified Ad-VP helper virus at MOI 10 (Ad-X unit/cell), and then super infected with the following recombinant parvovirus: hH-1-GFP, H-1-GFP, MVM-GFP or Chi-hH-1-GFP [23] at MOI of 0.1 GFU/cell or 0.5 for H-1-GFP. 1 day post-infection, medium was changed and three days later, cells were collected in their medium and lysed via three freeze and thaw cycles. Crude virus extracts were used to determine virus titers by transduction assay. Bars represent the mean values of three replicates (duplicates for H-1-GFP) with their relative standard deviations. Values above data bars show fold changes of virus titers produced in respect to the virus used as input. Viruses' titers are given as GFU/ml.

B: Ratio of produced replicative competent parvoviruses (RCV) in presence (+) versus absence (−) of Ad-VP helper conditions. RCV titers were measured by plaque assay on NBK cells and expressed in PFU/ml. GFU, green fluorescent unit; PFU, plaque forming unit.

Thus, in a first aspect the present invention relates to an adenovirus derived helper virus which may comprise the following adenoviral DNA sequences:

(a) an E2a gene;
(b) an E4(orf6) gene;
(c) an VAI RNA gene; and
(d) the parvovirus VP capsid gene unit.

DETAILED DESCRIPTION OF THE INVENTION

The adenovirus derived helper virus contains all DNA sequences of a helper virus which are necessary for forming parvoviruses, i.e., preferably only DNA sequences (a) to (d). Such DNA sequences are preferably derived from adenovirus 5. Suitable helper vector DNA sequences as a starting material for the preparation of the recombinant parvoviruses are described in German patent application 196 44 500.0-41, i.e., the Ad5 genes E2A, E4 and VA may be derived from the pDG plasmid and which are controlled by the respective original promoter or by a heterologous promoter.

The expression "adenovirus derived helper virus" used herein does not only relate to those with the original genes listed in (a) to (d) but also to viruses having modified genes, which include deletions or insertions of nucleotides, for example, but still encode proteins having the desired biological function. By means of common methods, a person skilled in the art may determine whether a modified gene still codes for a product having the desired biological function. The person skilled in the art also knows sources for the individual genes which are characteristic of the virus according to the invention. General methods known in this field may be used for the construction of the viruses which contain the above DNA sequences and, where appropriate, further sequences. These methods comprise e.g. in vitro recombination techniques, synthetic methods and in vivo recombination methods, as described in Sambrook et al., Molecular Cloning: A Laboratory Manual, $2^{nd}$ edition, Cold Spring Harbor Laboratory Press, Cold Spring Harbor N.Y. (1989), for example.

The expression "parvovirus VP capsid gene unit" used herein relates to the genes encoding VP1, VP2) and VP3 with VP3 being a cleavage product of VP2.

Preferably, the parvovirus VP capsid gene unit is under the control of a constitutive or inducible promoter active in mammals, and (c) a polyadenylation signal. The expression "a constitutive or inducible promoter active in mammals" used herein may comprise all of the promoters permitting in mammals the transcription of the desired DNA sequence, above all those resulting in a strong expression, preferably heterologous promoters. Suitable promoters are known to the person skilled in the art and comprise, e.g. the constitutive promoters CMV and cytokeratin K14 promoters or the inducible promoters MMTV (Mouse Mammary Tumor Virus), metallothionein and tetracycline-controllable promoter systems (Tet-on/-off).

In addition, the adenovirus derived helper virus or the recombinant parvovirus vector plasmid may contain a gene coding for a detectable phenotypic marker so as to prove the successful introduction into the target cell. Preferably, the marker protein is a fluorescent protein. This readily proves a transfection of the desired target cell. Examples of suitable genes coding for fluorescent proteins are rfp-(red), gfp-(green), cfp-(cyan) and yfp-(yellow) gene, rfp-(red) (DsredcDNA; Clontech) being preferred. Examples of suitable promoters for driving expression of the marker protein are RSV (rous sarcoma virus) promoter, CMV (cytomegalovirus) promoter and HSV (herpes simplex virus) tk promoters, the RSV promoter being preferred. The expression cassette (promoter/marker gene/polyadenylation site) is inserted in the vector(s) at a suitable site which may easily be determined by the person skilled in the art.

The term "parvovirus" as used herein encompasses all parvoviruses, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art; see, e.g., B. N. Fields et al., VIROLOGY, volume 2, chapter 69 (3d ed., Lippincott-Raven Publishers).

The genus Dependovirus contains the adeno-associated viruses (AAV), including but not limited to, AAV type 1, AAV type 2, AAV type 3, AAV type 4, AAV type 5, AAV type 6, avian AAV, bovine AAV, canine AAV, equine AAV, and ovine AAV; see, e.g., B. N. Fields et al., VIROLOGY, volume 2, chapter 69 (3d ed., Lippincoft-Raven Publishers).

Preferably, the "recombinant parvovirus vector lacking the VP1 and VP2 genes" has the following structure: TR—rep(NS1/NS2)—(optional: transgene)—TR [TR; Terminal Repeat].

In a second aspect, the present invention relates to a method of preparing a recombinant parvovirus characterized in that (i) mammalian cells are transfected with (a) a recombinant parvovirus vector lacking the VP1 and VP2 genes (but retaining the NS1/2 coding sequence, preferably under the control of the parvoviral P4 promoter), (b) a vector containing the genes encoding the parvovirus capsid proteins, and (c) an adenovirus derived helper vector which may comprise the adenoviral DNA sequences from the E2a gene, the E4(orf6) gene and an VA1 RNA gene; and (ii) the recombinant parvovirus is isolated from the mammalian cells or the medium after culturing the cells.

The helper vector may be any vector known in the art. Illustrative vectors include, but are not limited to, plasmids, naked DNA vectors, bacterial artificial chromosomes (BACs), yeast artificial chromosomes (YACs), and viral vectors. Preferred viral vectors include AAV, adenovirus, herpesvirus, Epstein-Barr virus (EBV), baculovirus, and retroviral (e.g., lentiviral) vectors, more preferably, adenovirus and herpesvirus vectors.

Recombinant parvovirus particles are produced by introducing the above vectors (a) to (c) into a permissive cell, as this term is understood in the art (e.g., a "permissive" cell may be infected or transduced by the virus). Any method of introducing the vectors into the permissive cell may be employed, including but not limited to, electroporation, transfection, calcium phosphate precipitation, microinjection, cationic or anionic liposomes, and liposomes in combination with a nuclear localization signal.

Any suitable permissive mammalian cell known in the art may be employed to produce the parvoviruses. Also preferred are trans-complementing packaging cell lines that provide functions deleted from a replication-defective helper virus, e.g., 293 cells, 911 cells, HeLa-E1 cells, 633 cells or other E1a trans-complementing cells.

In a preferred embodiment of the method of the invention, the mammalian cells are HEK 293 or HEK 293T cells.

In a third aspect, the present invention relates to a method of preparing a recombinant parvovirus characterized in that (i) mammalian cells are infected with (a) a recombinant parvovirus lacking the VP1 and VP2) genes (but retaining the NS1/2 coding sequence, preferably under the control of the parvoviral P4 promoter), and (b) the adenovirus derived helper plasmid of the invention, and (ii) the recombinant parvovirus is isolated from the mammalian cells or the medium after culturing the cells.

With the new adenovirus derived helper virus of the invention (Ad-VP helper virus) a protocol based only on infection may be used, bypassing the need of transfection. This opens the possibility of performing the production of the parvovirus in cell lines that are difficult to transfect but are more permissive to parvovirus replication than HEK 293T, e.g. NBK cells. Accordingly, in a preferred embodiment of this method of the invention the mammalian cell line is NBK. Other examples of cell lines that could be used for this application, are NB-E, SiHa or A9.

Preferably, the recombinant parvovirus is derived from parvovirus H-1 or MVM.

In a preferred embodiment of the methods of the invention, in the recombinant parvovirus vector the VP1 and VP2 genes are replaced by a transgene, i.e., a heterologous gene that is flanked by at least one TR.

Preferably, the transgene is under the control of the autologous P38 promoter of the H-1PV or autonomous parvovirus minute virus of mice which is strongly transactivated by the nonstructural protein NS1, a sequence-specific DNA-binding protein.

Preferably, the transgene is a gene encoding
(a) a marker protein, e.g., a protein described above; or
(b) a therapeutic gene, e.g., a cytotoxic polypeptide, cytokine or chemokine, or immunogenic polypeptide (for use as a vaccine; tumour suppressors, or RNA interference molecules and/or RNAi expressing cassettes (antisense oligonucleotides, siRNAs, shRNAs, miRNAs etc).

The present invention also provides a recombinant parvovirus obtainable by a method of the invention as well as a cell containing such recombinant parvovirus.

Finally, the present invention also relates to a pharmaceutical composition containing the recombinant parvovirus of the invention and a pharmaceutically acceptable carrier as well as the use of a recombinant parvovirus of the invention for use in gene therapy or a method of treating a tumor. Suitable carriers and the formulation of such medicaments are known to the person skilled in the art. Suitable carriers comprise e.g. phosphate-buffered saline solutions, water, emulsions, e.g. oil/water emulsions, wetting agents, sterile solutions, etc. The kind of carrier depends on how to administer the helper vector and recombinant parvovirus according to the invention. A suitable dosage is determined by the attending physician and depends on various factors, e.g. the patient's age, sex and weight, the severity of the disease, the kind of administration, etc.

A gene therapy may be carried out with recombinant parvovirus particles prepared with a helper vector according to the invention, the cells being transduced/infected by incubation with the viral particles. The cells may be present in an organism, the cells to be infected being reachable by needle injection, jet injection or particle gun. On the other hand, the cells to be transduced may also be isolated from an organism, be infected outside the organism and then be returned to the organism again. Such cells are referred to as autologous cells. Moreover, as to the organism it is also possible to use allogenic cells for the transduction. In this connection, it is favorable for these cells to belong to an HLA type corresponding to the organism. The person skilled in the art knows methods of providing cells with a certain HLA type. The recombinant parvovirus (particles) according to the invention are also useful for the adjuvant application to chemotherapy, i.e. to tumor therapy.

The usage of Ad-VP helper is not restricted to the production of recombinant parvoviruses. It may also be used in combination with recPV in cancer therapy. This would allow a second round of recPV replication at the tumor site increasing the parvovirus therapeutic efficacy. In addition, a second anti-cancer transgene may be inserted into the Ad-VP helper further increasing the therapeutic potential of the co-treatment.

Thus, the present invention also relates to a (pharmaceutical) composition which may comprise a helper virus according to the invention and a recombinant parvovirus. Preferably, both components contain (different) transgenes encoding therapeutic polypeptides, e.g., anti-cancer polypeptides.

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

Example 1

Materials and Methods (A) Cells

HEK 293T and NB324K (NBK) cells were cultivated in Dulbecco's modified Eagle medium (DMEM) or modified Eagle medium (MEM) respectively, supplemented with 10% (DMEM) or 5% foetal bovine serum (MEM), 2 mM L-Glutamine, 100 U/ml Penicillin and 100 µg/ml Streptomycin. Cells were maintained at 37° C. in 5% $CO_2$ and 92% of humidity.

(B) Plasmids and Viruses pH-1-EGFP was obtained by subcloning the EGFP gene, from pChi-hH-1-EGFP [23] into the psr19-H-1-Δ800 [2] using SacI/NotI restriction sites. phH-1-Luc is the phH1Δ1600luc described in [2].

The purified Ad-GFP virus was a kind gift from Dr. Laurent Mailly (Institut de Virologie, Inserm U748, Strasbourg, France) and was titrated on HEK 293T cells in green fluorescent unit per ml [GFU/ml] on the basis that one GFU is able to render green one 293T cell within 48 h.

Figure 7:
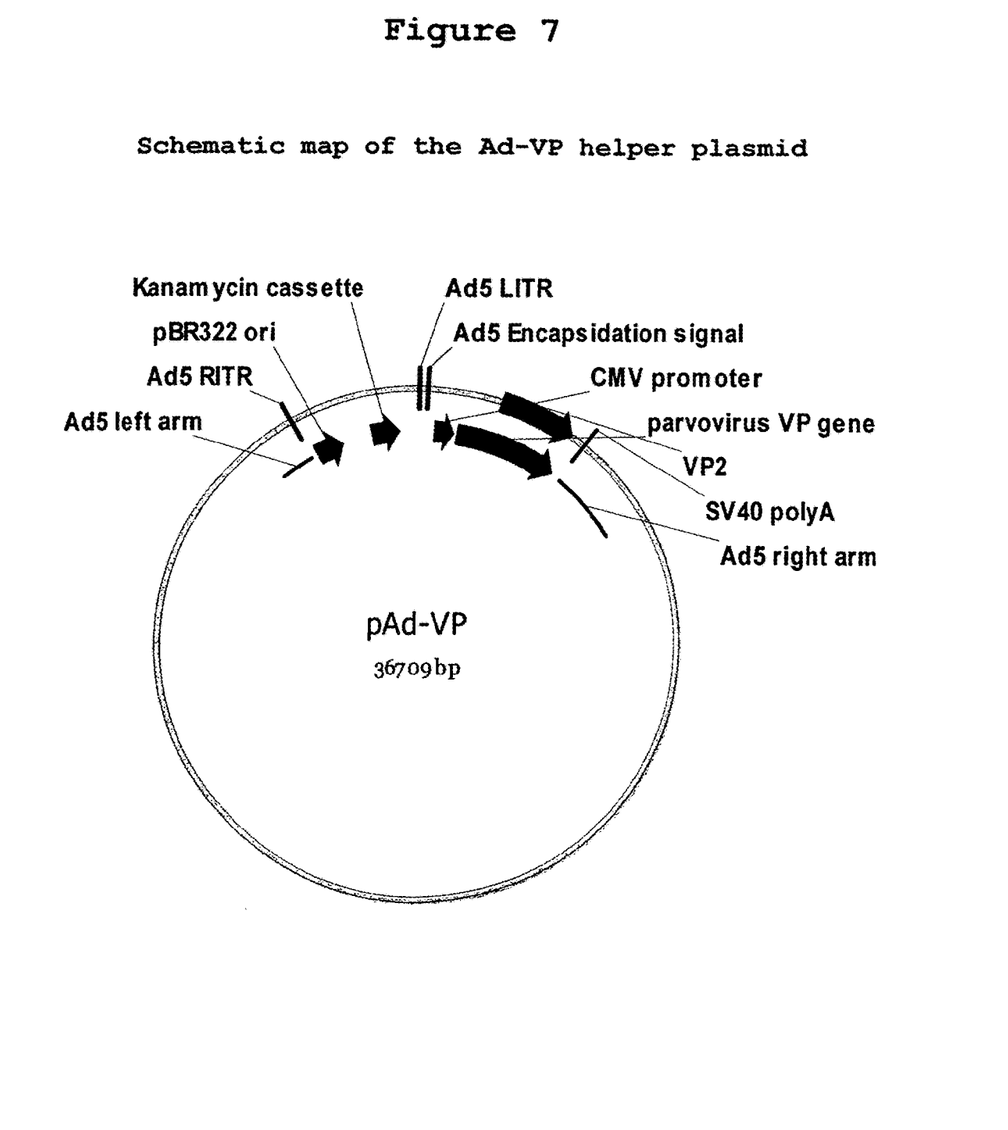
FIG. 7: Schematic map of the Ad-VP helper plasmid

The pAd-VP helper plasmid (a schematic map of this vector is provided in FIG. 7) was generated using AdEasy™ Adenoviral Vector System (Agilent technologies, Stratagene products, Waldbronn, Germany) by re-combining the pAd5ΔE1ΔE3 [24] and the pShuttle-CMVNP(H-1) vectors into BJ5183 bacteria, according to the manufacturer instructions. pShuttle-CMV/VP(H1) was generated by subcloning the VP region from the pcDNA5-CMVNP(H-1) using PmeI digestion, and relegating it into an EcoRV digested pShuttle-CMV vector (Agilent technologies, Stratagene products). pcDNA5-CMVNP(H-1) was generated by subcloning the VP region from pVP-sub into pcDNA5/FRT/TO (Invitrogen, Karlsruhe, Germany) using BamHI/XhoI restriction sites. pVP-sub was constructed by first inserting a HpaI restriction site into the polylinker of the pBluescript SK plasmid (pBSK, Stratagene), and then by subcloning into it the 2647-4680nt fragment of the H-1PV genome, containing the VP gene unit, from the p(BK)CMV/VP(H-1) plasmid [2], using HindIII/HpaI restriction sites.

Ad-VP helper virus was classically produced with 3 rounds of production in HEK 293T, then purified through a double CsCl gradient and titrated using Adeno-X™ Rapid Titer Kit (Clontech, Saint-Germain-en-Laye, France).

(C) Transfection

For the experiments shown in FIGS. 1, 3, 4, and 5, transfections were carried out using Fugene HD (Roche Diagnostics & Applied Sciences, Mannheim, Germany) according to the manufacturer's instructions with minor modifications. Plasmids were diluted in serum-free medium to a final concentration of 20 ng/µl. Fugene HD was then added with a 1:2.5 ratio (µg DNA:µl Fugene) and the mixture was incubated at RT for 30-60 min. Subsequently, the mixture was added to cells dropwise. For FIG. 2, the transfection was performed using polyethylenimine (PE1) (Sigma-Aldrich Chemie Gmbh, Munich, Germany), as described in [25].

For 6 cm dish format, $8 \times 10^5$ 293T cells per dish were seeded. One day later, cells were transfected with the following amounts, only when mentioned: 1.2 µg recombinant parvovirus vector, 2.4 µg pCMV/VP, 3 µg pXX6, 5.2 µg pAd5ΔE1ΔE3 and 3 or 5.2 µg of pFRTI/lacZeo (Invitrogen), used as control filler DNA. In 10 cm dish format and 175 cm² flask, cell number and plasmid quantities were proportionally adjusted and multiplied by factors of 2.5 and 6, respectively.

(D) Antibodies

The following antibodies were used for Western blot analysis: polyclonal anti-NS1 SP8 antiserum (a kind gift from Dr. Nathalie Salomé, DKFZ, Heidelberg, Germany), rabbit polyclonal anti-GFP (Santa Cruz, Heidelberg, Germany) and mouse monoclonal anti-actin (Clone C4, MP Biomedicals, Illkirch, France).

(E) Luciferase Assay

Luciferase Assay System (Promega, Mannheim, Germany) was used. $2.5 \times 10^4$ NBK cells per well were seeded in 48-well plates and infected on the next day with 0.1 ml of different dilutions of crude viral extracts. 48 h post infection, cells were washed with PBS and lysed with 100 µl of 1× passive lysis buffer. 10 µl of the cell lysates were mixed with 50 µl of luciferase substrate and the resulting luminescence was measured for 10 sec using the luminometer Fluoroskan (Ascent FL, Thermo Labsystems, Dreieich, Germany)

(F) Virus Titration

Transduction Assay $2.5 \times 10^4$ NBK cells per well were seeded in 48-well plates and infected on the next day with 0.1 ml of different dilutions of crude viral extracts. 72 h post infection, GFP-positive cells were counted using a fluorescent microscope. Virus titer in transduction unit per ml [TU/ml] was calculated as following: number of green cells×dilution factor× 10.

Quantitative Real Time Polymerase Chain Reaction (qPCR)

Crude virus extracts were digested with Benzonase® Nuclease Ultrapure grade (Sigma) (50 U/ml, 37° C. for 30 min) to remove genomic DNA and remaining transfected plasmids. To release viral DNA from viruses, 10 µl of each sample were lysed in a total of 40 µl of alkaline lysis buffer (1 M NaOH in TE buffer) at 56° C. for 30 min. Lysis was stopped by adding 960 µl of 40 mM HCl.

Quantification of viral DNA was carried out by real-time qPCR with a NS1-specific TaqMan™ probe (Applied Biosystems, Darmstadt, Germany), using an ABI Prism 7700 thermal cycler (Applied Biosystems) and analyzed by means of SDS 2.1 software (Applied Biosystems). Briefly, parvovirus DNA was amplified and detected using an NS1 specific 5'FAM-MGB3' labeled TaqMan™ probe. A plasmid containing the NS1 sequence was serial diluted in the range of $10^1$-$10^8$ copies/reaction and was used to standardize the qPCR. Individual reaction mixtures (20 µl) consisted of 1× TaqMan Universal PCR Master Mix™ (Applied Biosystems), 0.3 µM labelled NS1-TaqMan™ probe, 0.3 µM of each primer and 3 µl of template.

Viral DNA Hybridization Assay

NBK cells were seeded in 6 cm dishes with a density of $5 \times 10^5$ cells per dish. Next day, crude virus extracts were serial diluted at $10^{-4}$-$10^{-7}$ (in 1:10 steps) then used to infect the NBK cells in a total volume of 400 µL. After 1 h incubation at 37° C. and plates shaking every 10 min, 5 ml of medium was added to every dish. 72 h post infection, cell layers were washed with PBS and nitrocellulose filters of 25 mm diameter (Schleicher & Schuell, Dassel, Germany) were applied on top of the cells and moisturized with 100 µl of PBS. The filters were subsequently put upside down on Whatman paper saturated with denaturation buffer (0.5 M NaOH and 1.5 M NaCl). After 5 min, filters were transferred to Whatman paper saturated with neutralising buffer (0.5 M Tris/HCl (pH 7.2), 1.5 M NaCl and 1 mM EDTA). 5 min later, DNA was fixed by baking the filters at 80° C. for 2 h. Prehybridization was performed in 3×SSC (1×SSC is 0.15 M NaCl plus 0.015 M sodium citrate), 1% SDS, 5 mM EDTA, 10×Denhardt's solution and 100 µg/ml salmon sperm DNA at 65° C. for 1 h. Hybridization was made by the addition of the radioactive probe corresponding to the EcoRV (nt 385)-EcoRI (nt 1084) fragment of pMVM plasmid, purified by agarose gel electrophoresis, and labeled with [$^{32}$P]dCTP using the Megaprime DNA Labelling System (GE Healthcare, Munich, Germany). After incubating at 65° C. over night, filters were washed with washing buffer 1 (3×SSC (pH 7), 1% SDS) at 65° C. for 30 min and then with washing buffer 2 (0.3×SSC (pH 7) at 65° C. for 30 min. Subsequently, filters were placed on Whatman paper, wrapped in plastic foil and exposed to a radiographic film at −80° C. over night. Infected cells present black dots on the film due to the radioactively labeled viral DNA. Virus titers in replication units (RU) per ml [RU/ml] were calculated as following: number of black dots×dilution factor×7.5.

Plaque Assay

NBK cells grown in monolayer were infected with serial dilutions of crude virus extracts for 1 h, followed by replacement of the inoculum with a Bacto™ Agar (Becton Dickinson GmbH, Heidelberg, Germany) overlay (0.68% in Minimum Essential Medium [+] L-Glutamine (Gibco, Invitrogen), 5% FBS, 2 mM L-Glutamine, 100 U/ml Penicillin, 100 µg/ml Streptomycin. 5 days post infection, living cells were stained for 18 h by addition of neutral-red (0.2 mg/ml)-containing Bacto™-agar (0.85%) diluted in PBS. Plaques were counted and titers were expressed as plaque-forming units (PFU) per ml.

(G) DNA Extraction and Southern Blotting

For analyses of the viral DNA intermediates produced during recombinant virus production, cell extracts were prepared in a mixture (1:1) of vTE buffer (10 mM Tris-HCl [pH 8.7], 1 mM EDTA) and 2× Hirt buffer (20 mM Tris [pH 7.4], 20 mM EDTA, 1.2% SDS) and then digested with proteinase K (400 µg/ml) for 18 h at 46° C. under a rotation of 60 round per min. DNA was then sheared by several passages through 0.5- and 0.4-µm needles, subjected to phenol-chloroform extraction, and finally to DpnI digestion to remove bacterial plasmids harboring viral genomes.

DNA samples (2 µg) were fractionated through 1% agarose gel electrophoresis. After in gel DNA denaturation and neutralization, DNA was transferred onto Hybond-N nylon membrane (GE Healthcare) through a classical southern transfer procedure, then UV cross-linked to the membrane. The viral intermediates present on the membrane were then revealed with the same procedure used for the filters of viral DNA hybridization assay.

Example 2

Adenovirus Genes Increase Recombinant Parvovirus Production

In this study, it was investigated whether adenoviral genes are able to increase recombinant parvovirus production. To this end, HEK 293T cells were transiently co-transfected with a recombinant parvovirus plasmid carrying the GFP transgene (prec.PV-GFP), a plasmid encoding the H-1 parvovirus capsid proteins (pCMV/VP) and the adenovirus 5-derived plasmid, pXX6. pXX6 contains E2a, E4(orf6) and the VAI RNA adenoviral genes and is sufficient to promote AAV production [17, 18].

Figure 1:
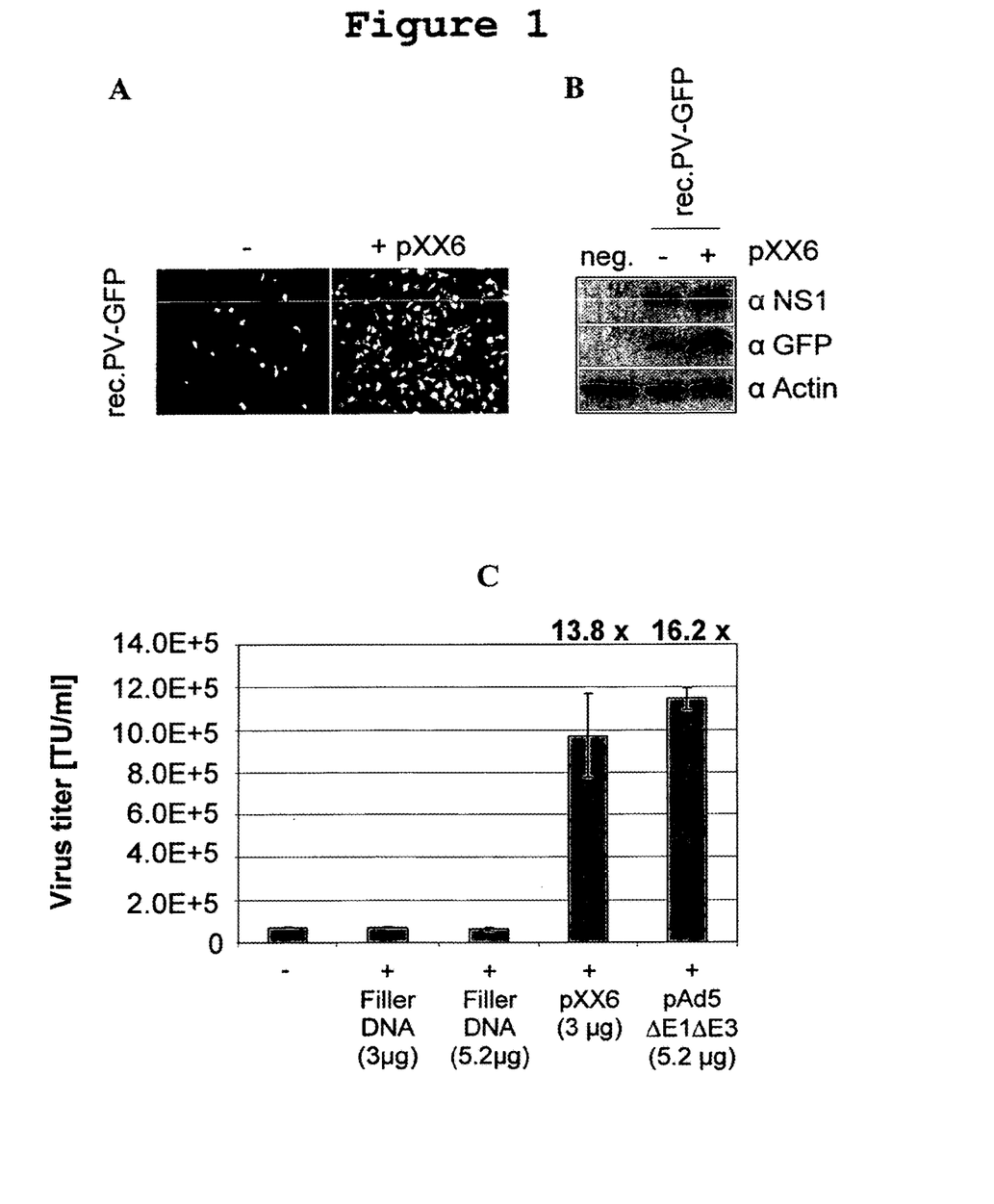
FIG. 1: Adenovirus-based plasmids enhance recombinant parvovirus production

Three days post transfection, cells were lysed and rec.PV-GFP viral production was assessed by transduction assay, as described in Example 1. So, cellular extracts from these virus-producing cells were used to inoculate fresh NBK cells. After 48 hours, GFP positive NBK cells were monitored by fluorescence microscopy (FIG. 1A). Extracts from cells transfected with pXX6 and parvoviral plasmids led to a much higher number of positive green cells as compared to cells transfected with parvoviral plasmids only, demonstrating that lysates from the latter contained lower amounts of recombinant parvovirus. Western blot analysis confirmed higher levels of GFP protein, together with higher levels of parvovirus NS1, in NBKcells infected with extracts obtained in the pXX6 condition (FIG. 1B).

To investigate whether the production of recombinant parvoviruses may be further improved with the presence of additional adenoviral elements, the effects of pXX6 and a more complete pAd5ΔE1ΔE3 vector in boosting parvovirus production were compared. Three days post transfection, viral transduction assays were performed as described above. As shown in FIG. 1C, both pAd5ΔE1ΔE3 and pXX6 significantly increase virus production by more than 10 fold in comparison to the negative control or filler conditions. The adenovirus helpers permitted to reach $10^6$ green transduction units (TU) per ml, corresponding to an average of 5 TU per seeded producer cell. Both pAd5ΔE1ΔE3 and pXX6 led to a comparable increase of recombinant parvovirus production under these experimental conditions, indicating that the genetic material contained in pXX6 is sufficient to induce this effect.

Figure 2:
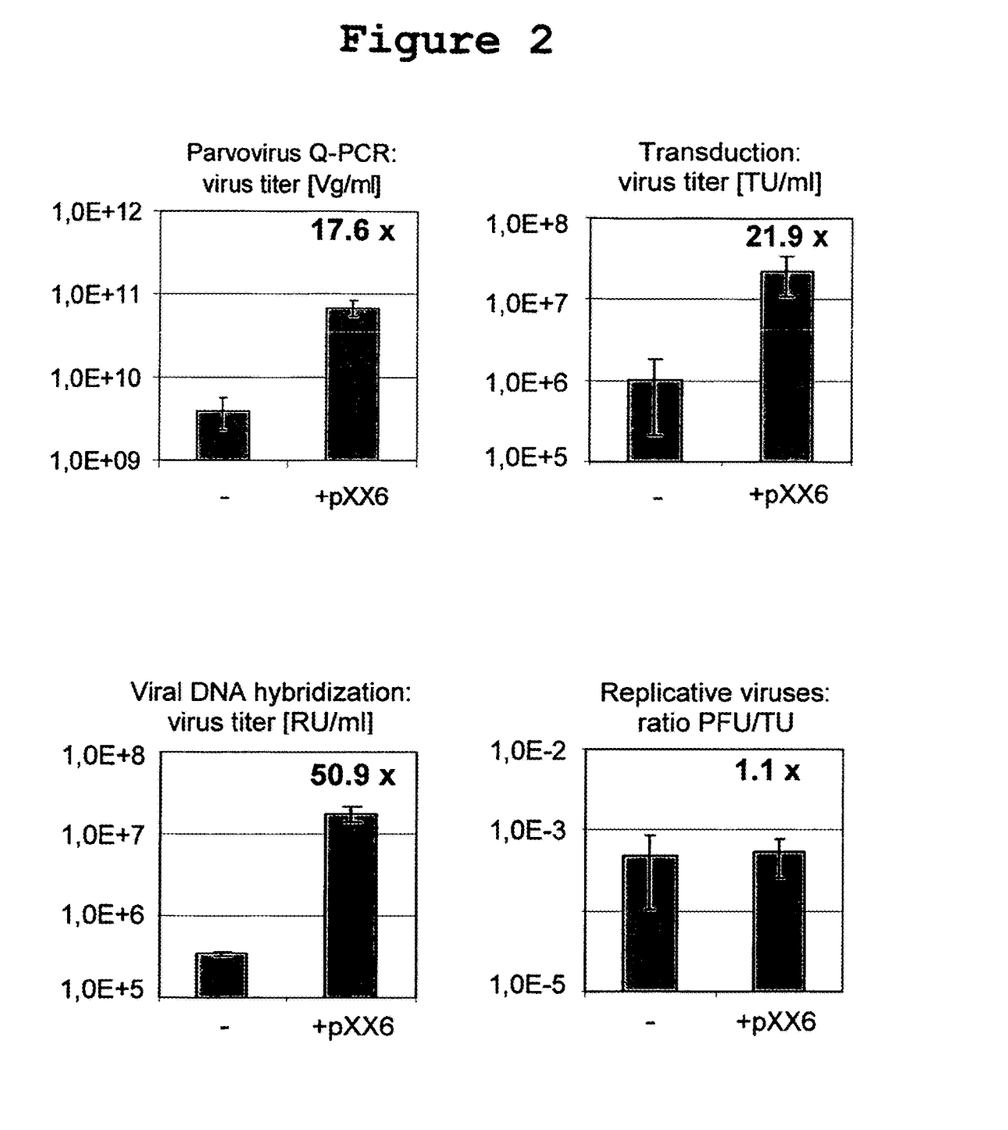

To carefully quantify the amounts of recombinant parvovirus produced with the help of pXX6, HEK 293T cells were seeded into 175 cm$^2$ flasks then co-transfected with prec.PV-GFP, pCMV/VP and with or without pXX6. Three days post transfection, cells were lysed in vTE buffer (see FIG. 2 legend). Produced viruses, contained in the cellular lysates, were directly quantified using a parvovirus-specific quantitative-PCR which measures the concentration of encapsidated parvovirus genome, expressed as viral genome (Vg) per ml. In addition, the cell lysates were used for infecting NBK indicator cells and virus titers were quantified by i) transductional assay, in which GFP-positive cells were counted and virus yields expressed as Transduction Unit (TU) per ml, and ii) a parvovirus-specific hybridization assay, in which number of cells sustaining viral DNA replication were detected using a NS-radiolabeled probe. The concentrations of the produced viruses are then expressed as Replication Unit (RU) per ml. FIG. 2 shows that all the different assays confirmed the significant increase of viral production in the presence of pXX6 plasmid.

Next, it was investigated whether pXX6 could lead to higher concomitant production of undesirable replication competent parvoviruses (RCV). RCVs were measured using a classical parvovirus plaque assay on NBK cells; the ratio of produced PFU per TU was not affected by pXX6 (FIG. 2, right panel) showing that pXX6 does not increase the productivity of RCV, therefore preserving the quality of the recombinant viruses produced.

To confirm the results shown in FIGS. 1 and 2, a similar experiment was conducted using another recombinant parvovirus, harboring a longer reporter transgene, prec.PV-Luciferase (prec.PV-Luc) (1656 nt insertion instead of 731 nt in the case of the previously used GFP transgene). Production of parvovirus harboring large transgenes (more than 800 nt) is known to be even less efficient than production with shorter ones (up to 800 nt) [2]. The ability of a different adenoviral helper plasmid, pVAE2AE4-5 to increase parvovirus production was also tested. This vector carries the same adenoviral genes as pXX6 in a different plasmid backbone [26]. Cells were co-transfected with pre-c.PV-Luc, pCMV/VP and with one of the adenovirus helper plasmids pXX6 or pVAE2AE4-5, or infected with Ad5ΔE1ΔE3-CMV/GFP (Ad-GFP) virus (at MOIs ranging from 0.1 to 5 GFU/cell (see FIG. 3)). Three days post transfection/infection, the yield of recombinant parvoviral production was estimated using a luciferase transduction assay.

Figure 3:
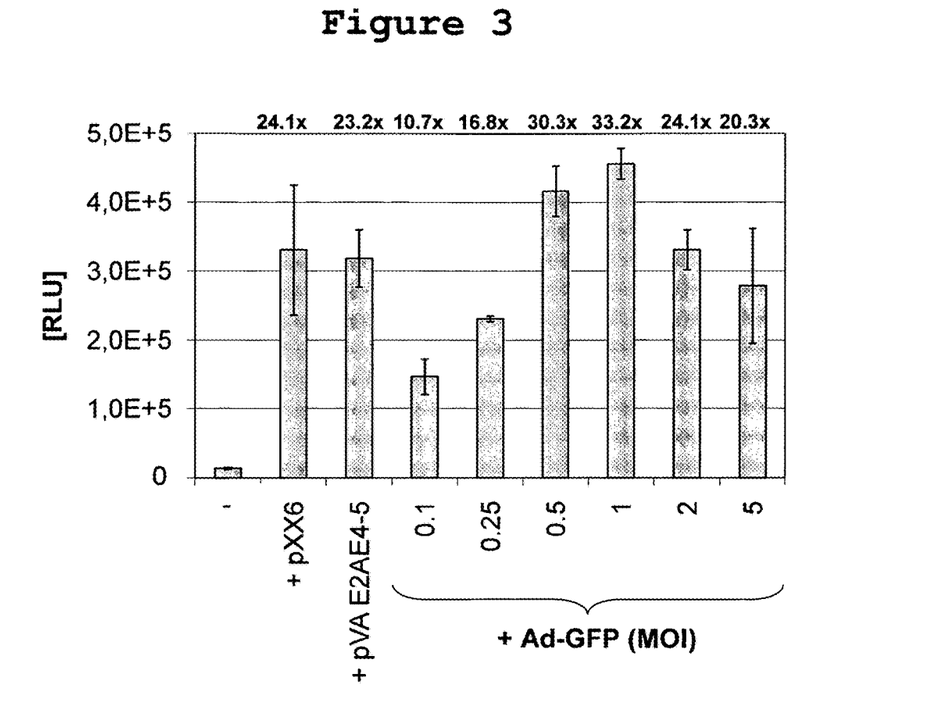

The results obtained in FIG. 3 confirm the boosting effect of pXX6 on recombinant parvovirus production (approximately 24 fold), generalizing the positive effects of this vector to other parvoviruses carrying different and longer transgenes. pVAE2AE4-5 increased parvoviral production to a similar extent, confirming that the elements responsible for the increase observed do lie within the common adenoviral sequences of pXX6 and pVAE2AE4-5 and not in the plasmid backbone. As infection with recombinant adenovirus also increased parvovirus production, the helper effects observed must be independent of the method chosen for introducing adenoviral genetic elements (by transfection or infection) into the producer cells. The highest increase of rec.PV-Luc production, (circa 30 fold), was obtained using Ad-GFP at MOI 1. Under these conditions, 100% of adenoviral GFP-transduction was observed in the producer cells, 2 days post infection. When Ad-GFP was used at MOIs 2 and 5, cellular toxicity was observed (data not shown), explaining why, under these conditions, lower parvovirus titers were obtained. The increase in production observed using adenovirus was slightly higher than with transfected helper plasmids, probably due to the higher rate of adenoviral transduction. Altogether, these results demonstrate that the presence of adenoviral genomic elements increases the production of recombinant parvoviruses.

Example 3 pXX6 Accelerates Recombinant Parvovirus Production

In a time course experiment it was investigated whether pXX6 affects the kinetics of virus production. Cells were first co-transfected with prec.PV-GFP, pCMV/VP with or without pXX6, and viral production was assessed at 12, 24, 48 and 72 h post transfection.

Figure 4:
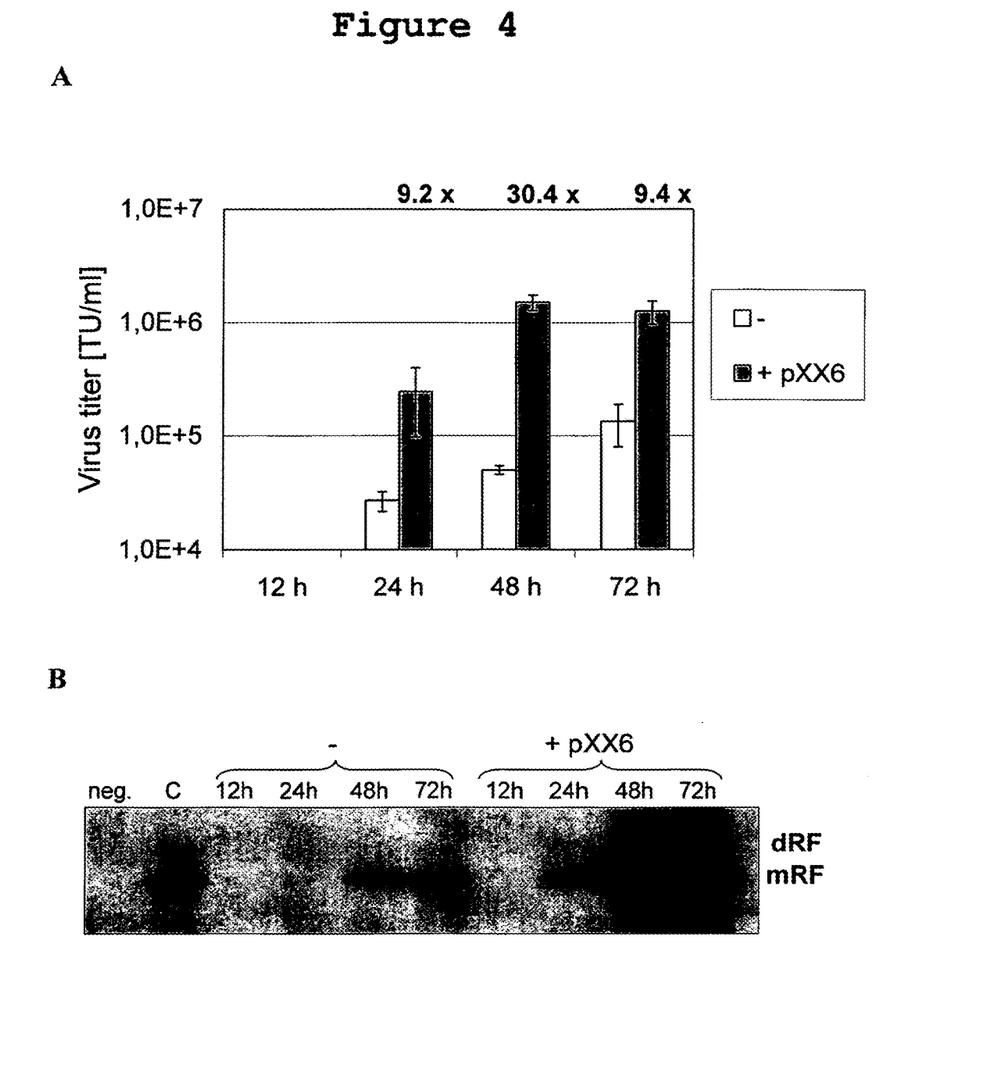
FIG. 4: pXX6 accelerates recombinant parvovirus production

As before, the presence of pXX6 greatly enhances recombinant parvovirus production (FIG. 4). This effect may be observed after 24 h (9.2 fold) but becomes more evident at 48 h (30.4 fold), when the production yield is maximal ($1.5 \times 10^6$ TU/ml). Virus production in the absence of pXX6 was much less efficient (maximal titer: $1.3 \times 10^5$ GFU/ml). It is worth mentioning that recombinant parvoviruses are usually harvested after 72 h of production.

Figure 6:
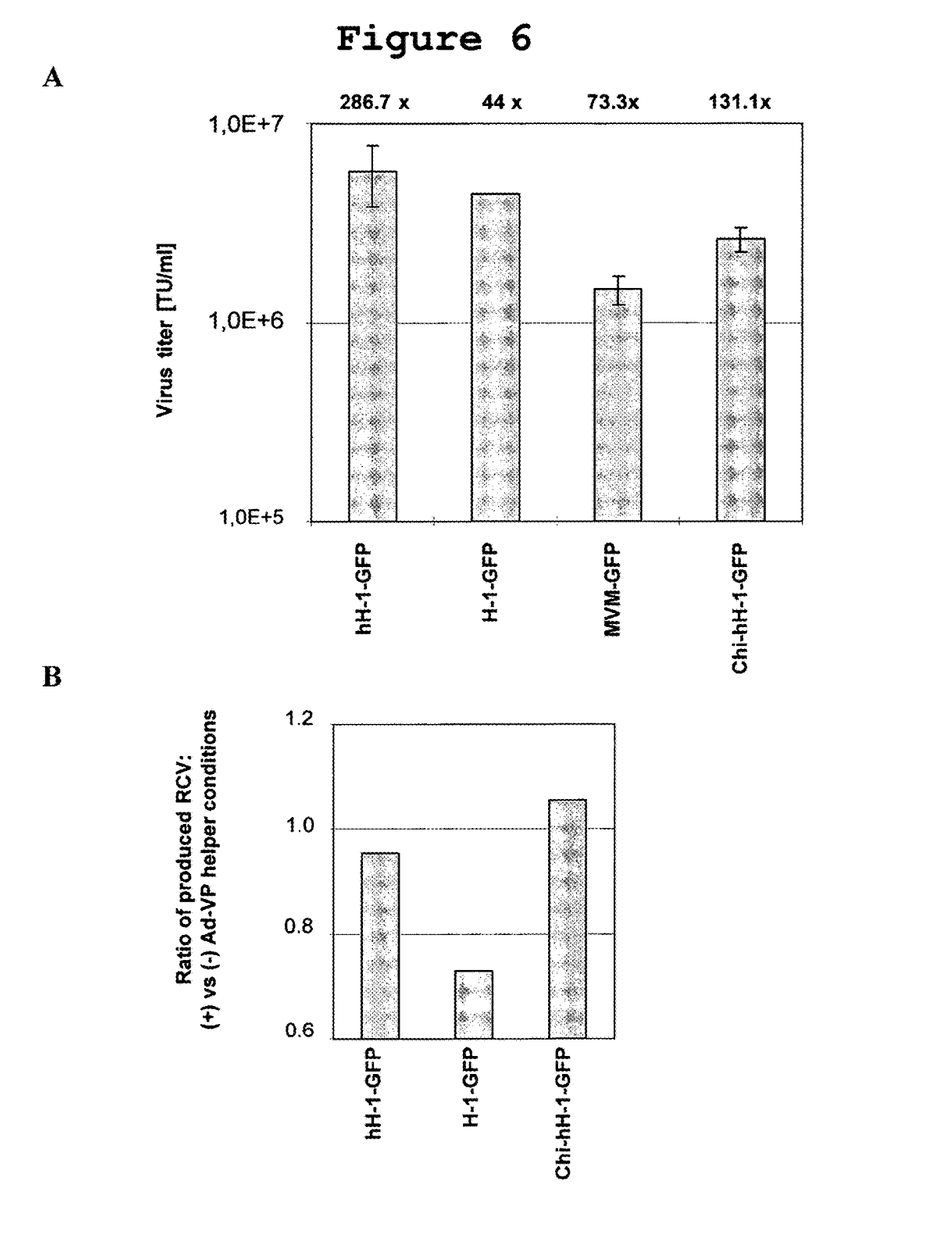

Thus, the use of adenoviral elements in recombinant parvovirus production increases the viral titers and decreases the production time by 24 h. Southern Blot (FIG. 6B) confirmed an increase in the amount of viral DNA produced in presence of pXX6, at 48 and 72 h post transfection. Monomeric replicative parvoviral DNA forms (mRF) were greatly enriched in pXX6 conditions, already detectable at 24 h and strongly enhanced at 48 h and 72 h. Dimeric replicative DNA forms (dRF) were only clearly detected in presence of pXX6 at 48 and 72 h production times. Thus pXX6 not only increases but also accelerates viral DNA replication.

Figure 5:
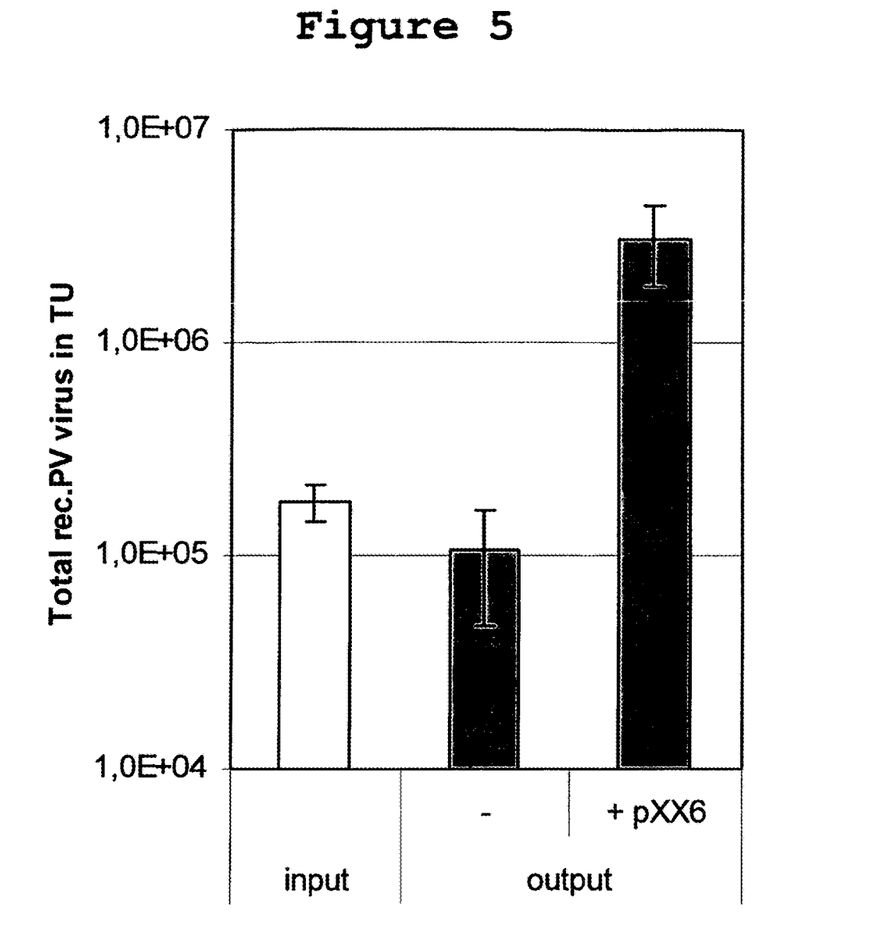

Example 4 pXX6 Also Increases Recombinant Parvovirus Production in a Transfection/Infection-Based Protocol Recombinant parvoviruses are routinely produced by co-transfecting the producer cells with two plasmids: one encoding the VP capsid proteins and a second containing the remaining parvovirus genome harboring the transgene of interest. As viral infection is a better gene delivery method than transfection, we aimed to replace as much as possible the transfection steps in our protocol by infection. A possibility would be to amplify recombinant parvoviruses by infecting permissive cells that have been transfected with the VP-containing plasmid. In this case, transfection would be limited only to the VP-plasmid while the parvovirus recombinant genome would be delivered through viral infection. Former experiments in the laboratory have, however, failed to produce recombinant parvovirus using this method. In light of the helper functions of pXX6, it was investigated whether the introduction of pXX6 could, in this case, rescue the production of recombinant parvoviruses. Cells were transfected with pCMV/VP in combination or not with pXX6 and then infected with rec.PV-GFP. Results showed a significant amplification of the viral dose used as inoculum (circa 17 fold) only in the presence of pXX6 plasmid results show that pXX6 (FIG. 5, and data not shown). These results show that pXX6 does not only support recombinant parvovirus production in a solely transfection-based protocol, but also when infectious parvoviral particles are used as a source of recombinant viral DNA. This supports the possible use of pXX6 in second-round-amplification of recombinant parvoviruses.

Example 5

Production of Recombinant Parvoviruses Using a Recombinant Ad-VP Helper Virus

To avoid the VP-plasmid transfection and allow virus amplification solely through co-infection with an helper virus it was tested whether it was possible to produce a recombinant parvovirus using an adenovirus that harbors not only the Ad genes needed to help parvovirus production but also the parvovirus VP capsid gene unit. The VP gene was cloned into the pAd5ΔE1ΔE3 [24], by recombination of pAd5ΔE1ΔE3 and pShuttle-CMV/VP, generating the pAd-VP helper construct. Ad-VP helper virus was classically produced in HEK 293T. Shape and titers of Ad-VP helper were similar to the ones of Ad5ΔE1ΔE3 virus, used as a control (data not shown).

With the new Ad-VP helper virus a protocol based only on infection may be used, bypassing the need of transfection. This opens the possibility of performing the production in cell lines that are difficult to transfect but are more permissive to parvovirus replication than HEK 293T, e.g. NBK cells.

NBK cells were seeded in 6 well plates and infected on the next day with purified Ad-VP helper and concomitantly with one of the following recombinant parvovirus: hH-1-GFP, H-1-GFP, MVM-GFP or Chi-hH-1-GFP. Three days after infection, cells were lysed and the recombinant viruses produced were titrated using transduction assay. As before, plaque assays were performed to control for production of replicative competent viruses.

Using this procedure, titers 2 to 5 fold higher than using transfection-based protocols as obtained in FIG. 1C were obtained (data not shown). Importantly this procedure did not increase the rate of RCV contamination in comparison to production carried out in the absence of Ad-VP helper. These results highlight the effectiveness of using the Ad-VP helper for the production of recombinant parvoviruses.

In conclusion, the Ad-VP helper procedure offers the following advantages: (i) it allows the production of recombinant parvovirus at high titers without affecting the quality of the viral stocks, (ii) it reduces the production time by 1 day (data not shown), (iii) it is only based on viral infection, bypassing the need of a transfection step, (iv) it allows production of recombinant parvoviruses in cell lines (e.g. NBK) which are more permissive than HEK 293T to parvovirus replication but could not be used before because difficult to transfect, and (v) it is a more economical process as it cuts the costs of transfection reagents, time and personnel.

LIST OF REFERENCES

1. Atchison, R. W., B. C. Casto, and W. M. Hammon, Adenovirus-Associated Defective Virus Particles. Science, 1965. 149: p. 754-6.
2. Kestler, J., et al., cis requirements for the efficient production of recombinant DNA vectors based on autonomous parvoviruses. Hum Gene Ther, 1999. 10(10): p. 1619-32.
3. Dupont, F., et al., Tumor-selective gene transduction and cell killing with an oncotropic autonomous parvovirus-based vector. Gene Ther, 2000. 7(9): p. 790-6.
4. Olijslagers, S., et al., Potentiation of a recombinant oncolytic parvovirus by expression of Apoptin. Cancer Gene Ther, 2001. 8(12): p. 958-65.
5. El Bakkouri, K., et al., In vivo anti-tumour activity of recombinant MVM parvoviral vectors carrying the human interleukin-2 cDNA. J Gene Med, 2005. 7(2): p. 189-97.
6. Haag, A., et al., Highly efficient transduction and expression of cytokine genes in human tumor cells by means of autonomous parvovirus vectors; generation of antitumor responses in recipient mice. Hum Gene Ther, 2000. 11(4): p. 597-609.
7. Wetzel, K., et al., Transduction of human MCP-3 by a parvoviral vector induces leukocyte infiltration and reduces growth of human cervical carcinoma cell xenografts. J Gene Med, 2001. 3(4): p. 326-37.
8. Wetzel, K., et al., MCP-3 (CCL7) delivered by parvovirus MVMp reduces tumorigenicity of mouse melanoma cells through activation of T lymphocytes and NK cells. Int J Cancer, 2007. 120(6): p. 1364-71.
9. Giese, N. A., et al., Suppression of metastatic hemangiosarcoma by a parvovirus MVMp vector transducing the IP-10 chemokine into immunocompetent mice. Cancer Gene Ther, 2002. 9(5): p. 432-42.
10. Enderlin, M., et al., TNF-alpha and the IFN-gamma-inducible protein 10 (IP-10/CXCL-10) delivered by parvoviral vectors act in synergy to induce antitumor effects in mouse glioblastoma. Cancer Gene Ther, 2009. 16(2): p. 149-60.
11. Brandenburger, A. and S. Russell, A novel packaging system for the generation of helper-free oncolytic MVM vector stocks. Gene Ther, 1996. 3(10): p. 927-31.
12. Chang, L. S., Y. Shi, and T. Shenk, Adeno-associated virus P5 promoter contains an adenovirus E1A-inducible element and a binding site for the major late transcription factor. J Virol, 1989. 63(8): p. 3479-88.
13. Carter, B. J., B. A. Antoni, and D. F. Klessig, Adenovirus containing a deletion of the early region 2A gene allows growth of adeno-associated virus with decreased efficiency. Virology, 1992. 191(1): p. 473-6.

14. Janik, J. E., et al., Efficient synthesis of adeno-associated virus structural proteins requires both adenovirus DNA binding protein and VA I RNA. Virology, 1989. 168(2): p. 320-9.
15. Fisher, K. J., et al., Transduction with recombinant adeno-associated virus for gene therapy is limited by leading-strand synthesis. J Virol, 1996. 70(1): p. 520-32.
16. Nayak, R. and D. J. Pintel, Adeno-associated viruses can induce phosphorylation of eIF2alpha via PKR activation, which can be overcome by helper adenovirus type 5 virus-associated RNA. J Virol, 2007. 81(21): p. 11908-16.
17. Grimm, D. and J. A. Kleinschmidt, Progress in adeno-associated virus type 2 vector production: promises and prospects for clinical use. Hum Gene Ther, 1999. 10(15): p. 2445-50.
18. Xiao, X., J. Li, and R. J. Samulski, Production of high-titer recombinant adeno-associated virus vectors in the absence of helper adenovirus. J Virol, 1998. 72(3): p. 2224-32.
19. Grimm, D., et al., Novel tools for production and purification of recombinant adenoassociated virus vectors. Hum Gene Ther, 1998. 9(18): p. 2745-60.
20. Guan, W., et al., The genome of human parvovirus b19 can replicate in nonpermissive cells with the help of adenovirus genes and produces infectious virus. J Virol, 2009. 83(18): p. 9541-53.
21. Ledinko, N. and H. W. Toolan, Human adenovirus type 12 as a "helper" for growth of H-1 virus. J Virol, 1968. 2(2): p. 155-6.
22. Fox, E., P. T. Moen, Jr., and J. W. Bodnar, Replication of minute virus of mice DNA in adenovirus-infected or adenovirus-transformed cells. Virology, 1990. 176(2): p. 403-12.
23. Wrzesinski, C., et al., Chimeric and pseudotyped parvoviruses minimize the contamination of recombinant stocks with replication-competent viruses and identify a DNA sequence that restricts parvovirus H-1 in mouse cells. J Virol, 2003. 77(6): p. 3851-8.
24. He, T. C., et al., A simplified system for generating recombinant adenoviruses. Proc Natl Acad Sci USA, 1998. 95(5): p. 2509-14.
25. Reed, S. E., et al., Transfection of mammalian cells using linear polyethylenimine is a simple and effective means of producing recombinant adeno-associated virus vectors. J Virol Methods, 2006. 138(1-2): p. 85-98.
26. Matsushita, T., et al., Adena-associated virus vectors can be efficiently produced without helper virus. Gene Ther, 1998. 5(7): p. 938-45.

The invention is further described by the following numbered paragraphs:

1. Adenovirus derived helper virus comprising the following adenoviral DNA sequences:
   (a) an E2a gene;
   (b) an E4(orf6) gene;
   (c) an VAI RNA gene; and
   (d) the parvovirus VP capsid gene unit.
2. The adenovirus derived helper virus of paragraph 1, wherein the expression of the parvovirus VP capsid gene unit is under the control of a CMV promoter.
3. A method of preparing a recombinant parvovirus characterized in that
   (i) mammalian cells are transfected with (a) a recombinant parvovirus vector lacking the VP1 and VP2 genes, (b) a vector containing the genes encoding the parvovirus capsid proteins, and (c) an adenovirus derived helper vector comprising the adenoviral DNA sequences from the E2a gene, the E4(orf6) gene and an VAI RNA gene; and
   (ii) the recombinant parvovirus is isolated from the mammalian cells or the medium after culturing the cells.
4. The method of paragraph 3, wherein the mammalian cells are HEK 293T cells.
5. A method of preparing a recombinant parvovirus characterized in that
   (i) mammalian cells are infected with (a) a recombinant parvovirus lacking the VP1 and VP2) genes, and (b) the adenovirus derived helper virus of paragraph 1 or 2; and
   (ii) the recombinant parvovirus is isolated from the mammalian cells or the medium after culturing the cells.
6. The method of paragraph 5, wherein the mammalian cells are NBK cells.
7. The method of any one of paragraphs 1 to 6, wherein the recombinant parvovirus is derived from H-1 or MVM.
8. The method of any one of paragraphs 1 to 7, wherein the adenoviral DNA sequences of the helper virus/vector are derived from Ad5.
9. The method of any one of paragraphs 3 to 8, wherein in the recombinant parvovirus vector the VP1 and VP2 genes are replaced by a transgene.
10. The method of paragraph 9, wherein expression of the transgene is under the control of the P38 promoter.
11. The method of paragraph 9 or 10, wherein the transgene is a gene encoding a marker protein.
12. The method of paragraph 9 or 10, wherein the transgene is a gene encoding a therapeutic or immunogenic polypeptide.
13. The method of paragraph 12, wherein the therapeutic protein is a cytotoxic polypeptide, cytokine and/or chemokine.
14. Recombinant parvovirus obtainable by a method of any one of paragraphs 3 to 13.
15. A cell containing the recombinant parvovirus of paragraph 14.
16. Pharmaceutical composition containing the recombinant parvovirus of paragraph 14 and a pharmaceutically acceptable carrier.
17. Recombinant parvovirus obtainable by a method of any one of paragraphs 3 to 13 for use in gene therapy or a method of treating a tumor.
18. A composition comprising the adenovirus derived helper virus/vector of paragraph 1 or 2, and a recombinant parvovirus.
19. The composition of paragraph 18, wherein the adenovirus derived helper virus, and the recombinant parvovirus contain a transgene.
20. A cell containing the composition of paragraph 19.
21. Use of a recombinant parvovirus obtainable by a method of any one of paragraphs 3 to 13 or the composition of paragraph 18 or 19 for the preparation of a pharmaceutical composition for gene therapy or for treating a tumor.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:
1. An isolated NB324K (NBK) cell comprising:
   (a) an adenovirus derived helper virus comprising:
      (i) adenoviral DNA sequences:
         (a) an adenoviral E2a gene;
         (b) an adenoviral E4(orf6) gene; and
         (c) an adenoviral VAI RNA gene; and
      (ii) a recombinant parvovirus VP capsid gene unit of H-1 or MVM; and

(b) a recombinant parvovirus derived from H-1 or MVM that lacks the VP1 and VP2 genes, wherein the NBK cell produces at least two fold higher an amount of recombinant parvovirus as compared to an NBK cell which does not comprise the adenovirus derived helper virus of (a).

2. The cell of claim 1, wherein the expression of the parvovirus VP capsid gene unit is under the control of a CMV promoter.

3. The cell of claim 1, wherein the adenoviral DNA sequences are derived from Ad5.

4. The cell of claim 1, wherein the adenovirus derived helper virus and the recombinant parvovirus contain a transgene.

5. The cell of claim 1, wherein in the recombinant parvovirus the VP1 and VP2 genes are replaced by a transgene.

6. The cell of claim 5, wherein expression of the transgene is under the control of the P38 promoter.

7. The cell of claim 5, wherein the transgene is a gene encoding a marker protein.

8. The cell of claim 5, wherein the transgene is a gene encoding a therapeutic or immunogenic polypeptide.

9. The cell of claim 8, wherein the therapeutic protein is a cytotoxic polypeptide, cytokine and/or chemokine.

* * * * *